(12) United States Patent
Sasaki et al.

(10) Patent No.: US 8,114,434 B2
(45) Date of Patent: *Feb. 14, 2012

(54) DICLOFENAC SODIUM PATCHES FOR TOPICAL TREATMENT OF PAIN

(75) Inventors: Yasuhiko Sasaki, Saitama (JP); Yukihiro Matsumura, Saitama (JP); Masaru Yamazaki, Saitama (JP); Hiroshi Arai, Gunma (JP); Shogo Kawabata, Saitama (JP); Masaaki Saito, Saitama (JP); Hirohisa Okuyama, Chiba (JP); Makoto Suzuki, Chiba (JP)

(73) Assignees: Tokuhon Corporation, Tokyo (JP); SSP Co., Ltd., Tokyo (JP); Dojin Iyaku Kako Co., Ltd., Tokyo (JP)

( * ) Notice: Subject to any disclaimer, the term of this patent is extended or adjusted under 35 U.S.C. 154(b) by 116 days.

This patent is subject to a terminal disclaimer.

(21) Appl. No.: 12/614,816

(22) Filed: Nov. 9, 2009

(65) Prior Publication Data

US 2010/0055160 A1 Mar. 4, 2010

Related U.S. Application Data

(63) Continuation of application No. 10/332,978, filed as application No. PCT/JP02/04942 on May 22, 2002, now Pat. No. 7,651,700.

(30) Foreign Application Priority Data

May 23, 2001 (JP) .................................. 2001-154008

(51) Int. Cl.
*A61F 13/00* (2006.01)
*A61F 13/02* (2006.01)
*A61L 15/16* (2006.01)
*A61K 9/70* (2006.01)

(52) U.S. Cl. ....................................... 424/449; 448/443
(58) Field of Classification Search .................. 424/449, 424/448, 443
See application file for complete search history.

(56) References Cited

U.S. PATENT DOCUMENTS

| | | | |
|---|---|---|---|
| 4,455,146 A | 6/1984 | Noda et al. |
| 4,738,848 A | 4/1988 | Yoshida et al. |
| 4,880,742 A | 11/1989 | Hayaishi et al. |
| 5,132,115 A | 7/1992 | Wolter et al. |
| 5,192,753 A | 3/1993 | McGeer et al. |

(Continued)

FOREIGN PATENT DOCUMENTS

EP 0 950 408 10/1999

(Continued)

OTHER PUBLICATIONS

U.S. Appl. No. 12/614,864, filed Nov. 9, 2009, Sasaki, et al.

(Continued)

*Primary Examiner* — Isis Ghali
(74) *Attorney, Agent, or Firm* — Oblon, Spivak, McClelland, Maier & Neustadt, L.L.P.

(57) ABSTRACT

The invention provides an analgesic anti-inflammatory patch of a hydrophobic type for topical application containing, in a Pressure Sensitive Adhesive(PSA), diclofenac sodium, pyrrolidone or a derivative thereof, a polyhydric alcohol fatty acid ester, and an organic acid. The patch exerts the following effects:
(1) diclofenac sodium is effectively and continuously released from a Pressure Sensitive Adhesive(PSA) and percutaneously absorbed, thereby attaining sustained, excellent pharmaceutical and pharmacological effects;
(2) the patch per se has high tackiness and safety; and
(3) diclofenac sodium remains stable in the Pressure Sensitive Adhesive(PSA).

14 Claims, 2 Drawing Sheets

U.S. PATENT DOCUMENTS

| | | |
|---|---|---|
| 5,332,577 A | 7/1994 | Gertner et al. |
| 5,474,985 A | 12/1995 | Polansky et al. |
| 5,554,650 A | 9/1996 | Holl et al. |
| 5,599,535 A | 2/1997 | Polansky et al. |
| 5,656,286 A | 8/1997 | Miranda et al. |
| 5,674,888 A | 10/1997 | Polansky et al. |
| 5,725,874 A | 3/1998 | Oda et al. |
| 5,994,401 A | 11/1999 | Cohen et al. |
| 6,001,875 A | 12/1999 | Cohen et al. |
| 6,262,121 B1 | 7/2001 | Kawaji et al. |
| 6,365,180 B1 | 4/2002 | Meyer et al. |
| 6,399,093 B1 | 6/2002 | Petrus |
| 6,569,463 B2 | 5/2003 | Patel et al. |
| 6,923,988 B2 | 8/2005 | Patel et al. |
| 6,991,095 B1 | 1/2006 | Yamasoto et al. |
| 7,615,237 B1 | 11/2009 | Takada et al. |
| 2002/0004065 A1 | 1/2002 | Kanios |
| 2002/0034539 A1 | 3/2002 | Esposito et al. |
| 2003/0129219 A1 | 7/2003 | Hong et al. |
| 2005/0250833 A1 | 11/2005 | Attali et al. |
| 2005/0272704 A1 | 12/2005 | Kelly |

FOREIGN PATENT DOCUMENTS

| | | |
|---|---|---|
| EP | 1 201 232 A1 | 5/2002 |
| GB | 2 362 825 A | 12/2001 |
| JP | 61-280426 | 12/1986 |
| JP | 04-193826 | 7/1992 |
| JP | 4-321624 | 11/1992 |
| JP | O5-178763 | 7/1993 |
| JP | 06-056660 | 3/1994 |
| JP | 6-205839 | 7/1994 |
| JP | 7-89853 | 4/1995 |
| JP | 9-143062 | 6/1997 |
| JP | 10-182440 | 7/1998 |
| JP | 10-182450 | 7/1998 |
| JP | 11-35458 | 2/1999 |
| JP | 2852816 | 2/1999 |
| JP | 11-222443 | 8/1999 |
| JP | 11-255644 | 9/1999 |
| JP | 2001-64205 | 3/2001 |
| KR | 2002-0009845 | 2/2002 |
| WO | WO 01/05381 A1 | 1/2001 |
| WO | WO 01/07018 A1 | 2/2001 |
| WO | WO 02/22109 A2 | 3/2002 |
| WO | WO 02/22109 A3 | 3/2002 |

OTHER PUBLICATIONS

Japanese Submission of Publications issued Nov. 30, 2010, in Patent Application No. 2001-154008 (with English-language translation).

Japanese Notice of Reasons for Rejection issued Dec. 14, 2010, in Patent Application No. 2001-154008 (with English-language translation).

Office Action issued Sep. 22, 2010, in Japan Patent Application No. 2001-154008 (with English-language Transaltion).

US 8,114,434 B2

DICLOFENAC SODIUM PATCHES FOR TOPICAL TREATMENT OF PAIN

This application is a Continuation of U.S. application Ser. No. 10/332,978, filed on Jan. 23, 2003, pending, which is a 371 of international application No. PCT/JP02/04942.

TECHNICAL FIELD

The present invention relates to a patch containing diclofenac sodium as an active ingredient, the patch exhibiting excellent releasability and percutaneous absorbability of diclofenac sodium and exerting a stable analgesic anti-inflammatory effect for a long period of time upon topical application.

BACKGROUND ART

Diclofenac sodium exerts excellent antipyretic, analgesic, and anti-inflammatory effects. Drug preparations containing diclofenac sodium are generally divided into peroral drugs exhibiting a systemic action and drugs for external use exhibiting a topical action. When a peroral drug is administered, grave, systemic adverse effects such as gastrointestinal disorders occur, thereby calling for further development of percutaneous-absorption-type patches for topical application for mitigating such adverse effects. In connection with a patch containing a non-steroidal analgesic anti-inflammatory drug such as diclofenac sodium, the most important issues are effective, sustained percutaneous absorption of the active ingredient into the disturbed portion directly under the patch and delivery of the active ingredient to the disturbed portion directly under the patch.

Since diclofenac sodium has considerably low solubility in water and an oily component, a wide range of studies have been carried out in order to stabilize it in a dissolved state in a drug for external use for promoting percutaneous absorption from a patch. For example, Japanese Patent Application Laid-Open (kokai) No. 61-280426 discloses incorporation of an organic acid (citric acid) as an additive for enhancing the solubility and percutaneous absorbability of diclofenac sodium. Japanese Patent Application Laid-Open (kokai) No. 4-193826 discloses incorporation of an essential oil component such as menthol or mentha oil as a percutaneous absorption promoter for diclofenac sodium. Japanese Patent Application Laid-Open (kokai) No. 5-178763 discloses incorporation of a polyhydric alcohol medium-chain fatty acid ester as a solubilizer for slightly soluble drugs. Japanese Patent Application Laid-Open (kokai) No. 11-222443 discloses incorporation of l-menthol and a pyrrolidone (pyrrolidone or at least one derivative thereof) as a percutaneous absorption promoter for diclofenac sodium.

However, percutaneous absorbability of a drug containing diclofenac sodium for external use is still unsatisfactory, and thus, there still remains a need for a drug for external use which promises more effective percutaneous absorption.

Thus, an object of the present invention is to provide a patch which exhibits excellent releasability and percutaneous absorbability of diclofenac sodium.

DISCLOSURE OF THE INVENTION

The present inventors have carried out extensive studies in order to solve the aforementioned problems, and have found that, by incorporating pyrrolidone or a derivative thereof, a polyhydric alcohol fatty acid ester, and an organic acid in combination into a Pressure Sensitive Adhesive (PSA) containing diclofenac sodium, there can be produced a patch of a hydrophobic type which attains a consistently dissolved state of diclofenac sodium in the PSA; exhibits excellent releasability of diclofenac sodium from the PSA and excellent percutaneous absorbability of diclofenac sodium; and exerts a stable analgesic anti-inflammatory effect for a long period of time.

Accordingly, the present invention provides an analgesic anti-inflammatory patch of a hydrophobic type for topical application containing, in a PSA, diclofenac sodium, pyrrolidone or a derivative thereof, a polyhydric alcohol fatty acid ester, and an organic acid.

BEST MODES FOR CARRYING OUT THE INVENTION

Figure 1:
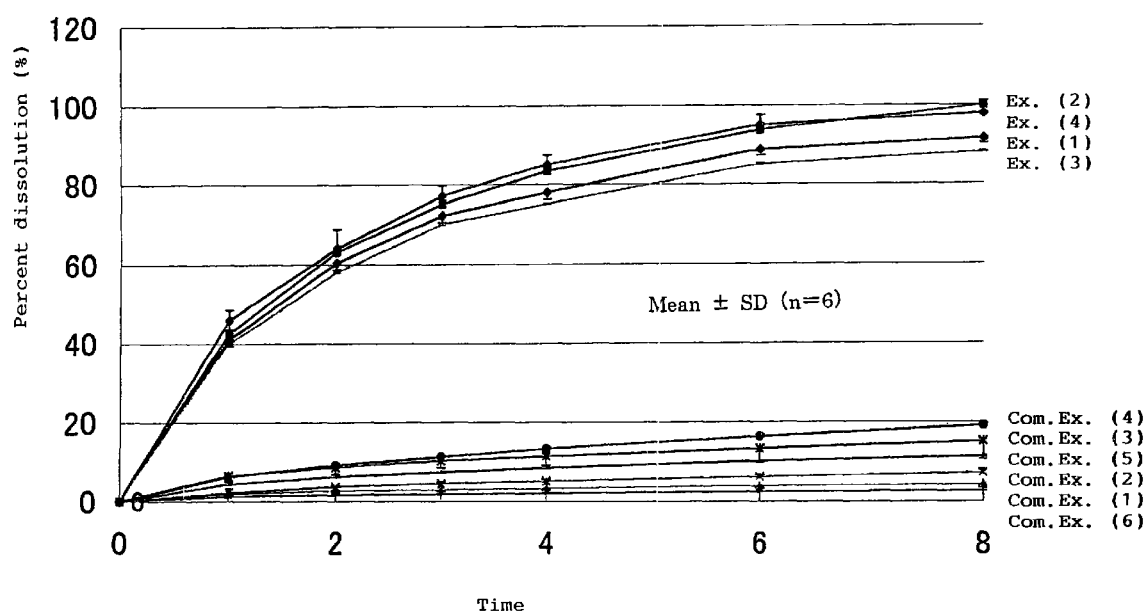
FIG. 1 is a graph showing dissolution of diclofenac sodium contained in tested patches.

The patch of the present invention contains, in a PSA, diclofenac sodium, pyrrolidone or a derivative thereof, a polyhydric alcohol fatty acid ester, and an organic acid. As mentioned above, diclofenac sodium is an active ingredient of the patch of the present invention. Preferably, diclofenac sodium is incorporated, as an active ingredient, into a PSA layer in an amount of 0.1-5.0 wt. %, more preferably 0.5-4.0 wt. %. From another viewpoint, diclofenac sodium is preferably incorporated into a PSA layer in an amount, per skin-contact area, of 5-2,000 μg/cm$^2$, more preferably 50-400 μg/cm$^2$. In the context of the present invention, the "PSA layer" does not include the support; i.e., the "PSA layer" refers to a layer containing the aforementioned ingredients and other ingredients in the PSA.

Examples of the above pyrrolidone or derivative thereof include 2-pyrrolidone and N-alkyl-2-pyrrolidones, with 2-pyrrolidone and N-methyl-2-pyrrolidone being particularly preferred. These pyrrolidone and derivetives thereof function as a solubilizer for diclofenac sodium, and each pyrrolidone species is preferably incorporated into a PSA layer in an amount of 0.5-8.0 wt. %, more preferably 1.0-5.0 wt. %.

Examples of the polyhydric alcohol fatty acid ester include alcohol (dihydric to tetrahydric) fatty acid esters; e.g., glycerin fatty acid esters, ethylene glycol fatty acid esters, propylene glycol fatty acid esters, sorbitan fatty acid esters, and pentaerythritol fatty acid esters. Specific examples include glycerin mono-(C6-C18) fatty acid esters, ethylene glycol mono-(C6-C18) fatty acid esters, propylene glycol mono-(C6-C18) fatty acid esters, sorbitan mono-(C6-C18) fatty acid esters, propylene glycol di-(C6-C18) fatty acid esters, and pentaerythritol tetra-(C6-C18) fatty acid esters. Of these, glycerin fatty acid esters (e.g., glyceryl tri(caprylate.caprate)), ethylene glycol fatty acid esters, pentaerythritol fatty acid ester (e.g., pentaerythrityl tetra-2-ethylhexanoate), and propylene glycol fatty acid esters (e.g., propylene glycol monocaprylate and propylene glycol dicaprylate) are more preferred. Of these, propylene glycol fatty acid esters are still more preferred. Examples of commercial products of these esters include Sefsol (product of Nikko Chemicals Co., Ltd.). These polyhydric alcohol fatty acid esters function as a percutaneous absorption promoter for diclofenac sodium and may be used in combination of two or more species. The ester is preferably incorporated into a PSA layer in an amount of 0.2-10.0 wt. %, more preferably 0.5-5.0 wt. %.

Examples of the organic acid include C3-C6 dicarboxylic acids and C3-C6 tricarboxylic acids. Of these, citric acid, tartaric acid, and succinic acid are preferred. These organic acids function as percutaneous absorption promoters for diclofenac sodium and may be used in combination of two or more species. The organic acid is preferably incorporated into a PSA layer in an amount of 0.05-4.0 wt. %, more preferably 0.1-2.0 wt. %.

As mentioned above, both the polyhydric alcohol fatty acid ester and the organic acid function as percutaneous absorption promoters for diclofenac sodium. The ratio by weight of the polyhydric alcohol fatty acid ester to the organic acid preferably falls within a range of 1:20 to 200:1, more preferably 1:4 to 50:1. The total amount of the polyhydric alcohol fatty acid ester and the organic acid incorporated into a PSA layer preferably falls within a range of 0.25-14 wt. %, more preferably 0.6-7 wt. %.

The PSA into which the above components are to be incorporated is formed from a PSA base and a tackifier in combination. A preferable PSA base is a styrene-isoprene-styrene block copolymer (SIS). The SIS is commercially available, and examples of commercial products include Cariflex TR-1107 and Cariflex TR-1117 (trade names; product of Shell Kagaku K.K.). The amount of the PSA base incorporated into a PSA layer preferably falls within a range of 10-50 wt. %, more preferably 10-40 wt. %.

Examples of the tackifier include rosin ester resin, polyterpene resin, terpene phenol resin, and petroleum resin. Of these, rosin ester resin is preferred, with a rosin ester resin which has been subjected to removal of low-boiling fractions and subsequent hydrogenation (e.g., Ester Gum HG, product of Arakawa Chemical Industries, Ltd.) being particularly preferred. YS Resin (polyterpene resin, product of Yasuhara Yushi Kogyo Co., Ltd.), YS Polyster (terpene phenol resin, product of Yasuhara Yushi Kogyo Co., Ltd.), Quintone (petroleum resin, product of Nippon Zeon Co., Ltd.), Arkon (petroleum resin, product of Arakawa Chemical Industries, Ltd.), Escorez (petroleum resin, product of Exxon Corp.), and other similar products may be used. The amount of the tackifier incorporated into a PSA layer preferably falls within a range of 5-50 wt. %, more preferably 5-30 wt. %.

The patch of the present invention may further contain arbitrary components such as an essential oil component (e.g., l-menthol or mentha oil); a softening agent (e.g., liquid paraffin); an antiageing agent; or a filler (inorganic compound). In addition to diclofenac sodium, the patch of the present invention may further contain another drug component such as ketoprofen, indomethacin, flurbiprofen, glycolyl salicylate, methyl salicylate, capsaicine, nonyl vanillylamide, tocopheryl acetate, a phellodendron bark extract, or an Aesculus Hippocastanum Seed extract. The softening agent is preferably incorporated into a PSA layer in an amount of 30-70 wt. %, more preferably 40-60 wt. %. The essential oil component is preferably incorporated into a PSA layer in an amount of 0.2-5.0 wt. %, more preferably 0.5-3.0 wt. %.

As mentioned above, the PSA layer included in the patch of the present invention is of hydrophobic type and contains substantially no water. This feature renders the present invention fundamentally different from that of conventional cataplasms.

The patch of the present invention can be produced by spreading the aforementioned PSA base on a soft support. Any type of support can be employed so long as the support is formed of a soft sheet which does not permit permeation of the PSA base through the back of the support. Examples of the sheet employable as the support of the present invention include woven and non-woven fabrics; plastic films such as polyolefin film, polyvinyl alcohol film, vinyl chloride film, urethane alloy film, urethane-vinyl chloride copolymer film, and ethylene-vinyl acetate film; film of a foamed blend of acrylic polymer or polystyrene-polybutadiene and polyisoprene; these films on which metal is coated through vapor deposition; and laminated sheets obtained from two or more species of these films. Appropriately, the support typically has a thickness of about 1,000 μm or less, preferably 30-700 μm.

The thus-produced patch of the present invention is applied to skin sites where an analgesic anti-inflammatory effect is needed; e.g., inflammation sites of the joints, muscles, neck, etc.

EXAMPLES

The present invention will next be described in more detail by way of examples, which should not be construed as limiting the invention thereto.

Examples 1 to 4

In each example, a PSA base and a softening agent shown in Table 1 were kneaded by use of a heating-kneader. A tackifier was added to the kneaded product, and the resultant mixture was further kneaded. Subsequently, diclofenac sodium was dissolved in a liquid mixture containing pyrrolidone, a polyhydric alcohol fatty acid ester, and citric acid, and the resultant solution was added to the above kneaded product. The resultant mixture was further kneaded, to thereby yield a uniform mixture. The mixture was applied to and spread on a support, to thereby form a PSA layer. After an appropriate period of time, the PSA layer was covered with a liner, and the resultant laminated product was cut into pieces of desired dimensions, to thereby obtain patches.

TABLE 1

|  | Ex. 1 | Ex. 2 | Ex. 3 | (wt. %) Ex. 4 |
| --- | --- | --- | --- | --- |
| PSA base |  |  |  |  |
| SIS | 28.5 | 28.5 | 38.0 | 30.0 |
| Polyisobutylene | 2.0 | — | — | 4.0 |
| Tackifier |  |  |  |  |
| Ester Gum HG*[1] | 12.0 | 12.0 | 20.0 | 25.0 |
| Softening agent |  |  |  |  |
| Liquid paraffin | 50.1 | 50.1 | 33.8 | 32.7 |
| Solubilizer |  |  |  |  |
| 2-Pyrrolidone | 4.0 | 4.0 | 2.0 | 1.0 |
| Absorption promoter |  |  |  |  |
| Sefsol*[2] | 2.0 | 2.0 | 4.0 | 3.0 |
| Citric acid | 0.4 | 0.4 | 0.2 | 0.3 |
| Tackiness regulator |  |  |  |  |
| l-Menthol | — | 2.0 | 1.0 | 3.0 |
| Drug ingredient |  |  |  |  |
| Diclofenac sodium | 1.0 | 1.0 | 1.0 | 1.0 |

*[1]Hydrogenated rosin ester resin (Arakawa Chemical Industries, Ltd.)
*[2]Glycerin fatty acid ester (Nikko Chemicals Co., Ltd.)

Test Example 1 (Dissolution Test)

The time-elapsed dissolution amount of diclofenac sodium released from each patch was determined through a paddle over disk method by use of a dissolution tester according to Japanese Pharmacopoeia. Specifically, each test patch was cut into pieces (5 cm×5 cm), and each piece was bonded to Teflon mesh. The piece was clamped by two pieces of watch glass and placed in a phosphate buffer (900 mL, pH: 7.2) at 32° C. A paddle was rotated 25 mm above the patch, and a liquid (1 mL) was sampled at an intermediate level between the bottom of the paddle and the liquid surface. The sampling was performed 0.5, 1, 2, 3, 4, 6, and 8 hours after paddle rotation. Diclofenac sodium contained in each sampled liquid was quantitated through high performance liquid chromatography.

The patches prepared in the above Examples 1 to 4 and those prepared in Comparative Examples were employed as test patches. Test patches of Comparative Examples were prepared in accordance with the formulations shown in Table 2 in a manner similar to those employed in Examples 1 to 4.

TABLE 2

| | Comp. Ex. 1 | Comp. Ex. 2 | Comp. Ex. 3 | Comp. Ex. 4 | Comp. Ex. 5 | (wt. %) Comp. Ex. 6 |
|---|---|---|---|---|---|---|
| SIS | 28.5 | 28.5 | 28.5 | 28.5 | 28.5 | 28.5 |
| Polyisobutylene | 2.0 | 2.0 | 2.0 | 2.0 | — | — |
| Ester Gum HG | 12.0 | 12.0 | 12.0 | 12.0 | 12.0 | 12.0 |
| Liquid paraffin | 54.0 | 50.0 | 54.5 | 56.1 | 58.5 | 52.5 |
| Pyrrolidone | — | 4.0 | — | — | — | 4.0 |
| Sefsol | — | — | 2.0 | — | — | 2.0 |
| Citric acid | — | — | — | 0.4 | — | — |
| 1-Menthol | 2.5 | 2.5 | — | — | — | — |
| Diclofenac Na | 1.0 | 1.0 | 1.0 | 1.0 | 1.0 | 1.0 |

Comp. Ex. 1: Patch disclosed in Japanese Patent Application Laid-Open (kokai) No. 4-198326
Comp. Ex. 2: Patch disclosed in Japanese Patent Application Laid-Open (kokai) No. 11-222443
Comp. Ex. 3: Patch disclosed in Japanese Patent Application Laid-Open (kokai) No. 5-178763
Comp. Ex. 4: Patch disclosed in Japanese Patent Application Laid-Open (kokai) No. 61-280426

Each of the thus-determined diclofenac sodium levels was converted to the corresponding percent dissolution from the patch (%). The results are shown in FIG. 1. In FIG. 1, "Mean," "SD," and "n" denote a mean value, a standard deviation, and the number of test samples, respectively.

The results indicate that the patches according to the present invention exhibit percent dissolution as high as four times or more that of all patches of Comparative Examples 1 to 6.

Test Example 2 (Transdermal Permeability Test)

Hairless rats (body weight: 170 g) were anesthetized by pentobarbital. After removal of hair from the abdomen, abdominal skin samples were extirpated. Each of the thus-extirpated skin samples was set in a vertical cell (effective permeation area: 2.83 $cm^2$, cell capacity: 16 mL), and a test patch (diameter: 1.9 cm) was attached to the skin sample. Subsequently, the receiver liquid in the cell was stirred by means of an electromagnetic stirrer while the cell was heated at 37° C. A portion (0.5 mL) of the receiver liquid was sampled a plurality of times at constant time intervals, and the diclofenac sodium content of the liquid portion was determined.

Figure 2:
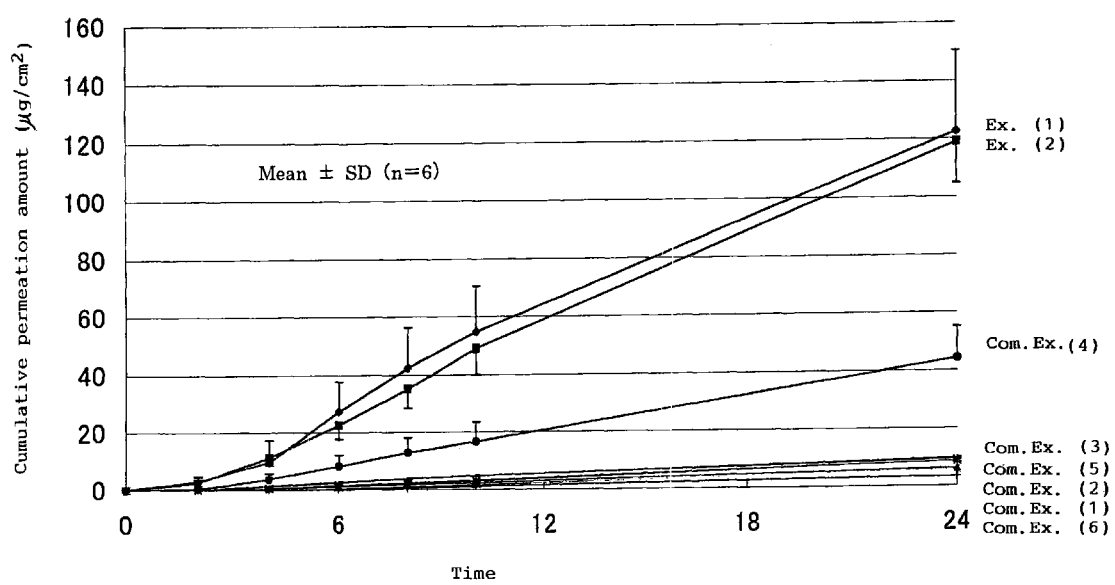
FIG. 2 is a graph showing transdermal permeability of diclofenac sodium released from tested patches.

FIG. 2 shows cumulative permeation amounts of diclofenac sodium that had been released from each patch sample and had permeated each extirpated skin sample of the abdomen of each rat (Examples 1 and 2 and Comparative Examples 1 to 6). As is clear from FIG. 2, the patches according to the present invention exhibit cumulative permeation amounts as high as about three times or more those of patches of Comparative Examples 1 to 6.

The results of Test Examples 1 and 2 indicate that the patch of the present invention can exhibit remarkably promoted releasability and percutaneous absorbability of diclofenac sodium which conventional techniques have not satisfactorily attained. Thus, the patch of the present invention has proven to be a clinically useful patch which mitigates systemic adverse effect and provides other advantages.

INDUSTRIAL APPLICABILITY

The patch of the present invention exerts the following effects:

(1) diclofenac sodium is effectively and continuously released from a PSA and percutaneously absorbed, thereby attaining sustained, excellent pharmaceutical and pharmacological effects;

(2) the patch per se has high tackiness and safety; and (3) diclofenac sodium remains stable in the PSA.

The invention claimed is:

1. A method of treating pain, comprising topically applying an analgesic anti-inflammatory Pressure Sensitive Adhesive (PSA) patch, comprising a soft support and a PSA layer on the soft support, to a subject in need thereof, wherein the PSA layer comprises
   1 wt. % of diclofenac sodium,
   2 to 4 wt. % of N-methyl-2-pyrrolidone,
   2 wt. % of propylene glycol monocaprylate,
   0.4 wt. % of citric acid,
   28.5 to 38 wt % of a styrene-isoprene-styrene block copolymer,
   2 to 4 wt % polyisobutylene,
   12 to 25 wt % of an ester gum,
   30 to 40 wt % of liquid paraffin, and
   no added water.

2. The method of claim 1, wherein the PSA layer further comprises 1-menthol.

3. The method of claim 2, wherein the PSA layer contains 1 to 3 wt .% of the 1-menthol.

4. The method of claim 1, wherein the PSA layer contains no 1-menthol.

5. The method of claim 1, further comprising an anti-ageing agent.

6. The method of claim 1, wherein the soft support does not permit permeation of the PSA layer through the back of the support.

7. The method of claim 1, wherein the soft support is selected from the group consisting of woven fabrics, non-woven fabrics, plastic films, and films of a foamed blend of acrylic polymer or polystyrene-polybutadiene and polyisoprene.

8. The method of claim 1, wherein the soft support is a plastic film selected from the group consisting of polyolefin film, polyvinyl alcohol film, vinyl chloride film, urethane alloy film, urethane-vinyl chloride copolymer film, and ethylene-vinyl acetate film.

9. The method of claim 8, wherein the plastic film is a film of foamed blend of acrylic polymer or polystyrene-polybutadiene and polyisoprene.

10. The method of claim 1, wherein the soft support has a thickness of about 1,000 μm or less.

11. The method of claim 1, wherein the soft support has a thickness of 30-700 μm.

12. The method of claim 1, wherein the patch is applied to the site of an inflamed joint.

13. The method of claim 1, wherein the patch is applied to an inflamed site of the neck of the subject.

14. The method of claim 1, wherein the patch is applied to an inflamed site of a muscle of the subject.

* * * * *